United States Patent
Howell et al.

(10) Patent No.: US 10,005,816 B2
(45) Date of Patent: Jun. 26, 2018

(54) PEPTIDES AND THEIR USE IN FOOD AND BEVERAGE

(71) Applicant: The Folger Coffee Company, Orrville, OH (US)

(72) Inventors: Jessalin Anise Howell, Mason, OH (US); James Cody Hanreck, Marshallville, OH (US)

(73) Assignee: THE FOLGER COFFEE COMPANY, Orrville, OH (US)

( * ) Notice: Subject to any disclaimer, the term of this patent is extended or adjusted under 35 U.S.C. 154(b) by 463 days.

(21) Appl. No.: 14/569,911

(22) Filed: Dec. 15, 2014

(65) Prior Publication Data

US 2016/0165916 A1    Jun. 16, 2016

(51) Int. Cl.

| | | |
|---|---|---|
| *A23F 5/24* | (2006.01) | |
| *C07K 7/06* | (2006.01) | |
| *A23L 2/56* | (2006.01) | |
| *A23F 5/40* | (2006.01) | |
| *A23L 27/00* | (2016.01) | |
| *A23L 27/21* | (2016.01) | |
| *A23L 27/22* | (2016.01) | |

(52) U.S. Cl.
CPC ............... *C07K 7/06* (2013.01); *A23F 5/405* (2013.01); *A23L 2/56* (2013.01); *A23L 27/21* (2016.08); *A23L 27/22* (2016.08); *A23L 27/88* (2016.08)

(58) Field of Classification Search
CPC ... C07K 7/06; A23L 2/56; A23L 27/88; A23L 27/21; A23L 27/22; A23F 5/405
See application file for complete search history.

(56) References Cited

U.S. PATENT DOCUMENTS

| | | | | |
|---|---|---|---|---|
| 7,390,874 | B2 * | 6/2008 | Aoki | C07K 7/06 426/45 |
| 2005/0143313 | A1 * | 6/2005 | Aoki | C07K 7/06 514/21.8 |
| 2005/0261197 | A1 * | 11/2005 | Aoki | A61K 31/353 514/12.2 |
| 2007/0022489 | A1 * | 1/2007 | McCarthy | C07K 14/8139 800/278 |
| 2011/0009345 | A1 * | 1/2011 | Aoki | A23L 33/18 514/21.8 |

FOREIGN PATENT DOCUMENTS

JP    63152946    *    6/1988

OTHER PUBLICATIONS

English Tranlsation for JP63152946 published Jun. 1988.*
Hyun-Ock Kim and Eunice C. Y. Li-Chan, Quantitative Structure-Activity Relationship Study of Bitter Peptides, Journal of Agricultural and Food Chemistry, Published on Web Nov. 22, 2006, J. Agric. Food Chem., vol. 54, No. 26, 2006.
Karl Heinz Ney, Bitterness of Peptides: Amino Acid Composition and Chain Length, ACS Symposium Series, Published Dec. 14, 1979, 0-8412-0526-4/79/47-115-149.

* cited by examiner

*Primary Examiner* — Anthony Weier
(74) *Attorney, Agent, or Firm* — Michael A. Olshavsky; Christopher L. Smith

(57) ABSTRACT

Described herein is a peptide with an amino acid sequence comprising a Leu-Leu moiety. Also described is a composition having a mixture of such peptides, and foods and beverages containing such compositions including, for example, roast and ground coffee, coffee brew, coffee creamer, and tea. The addition of one or more of these peptide(s) to coffee brews made from instant coffee, liquid coffee concentrate, or decaf coffee demonstrates that these peptides improve the taste profile of such coffee brews.

14 Claims, No Drawings

SEQUENCE LISTING

<160> NUMBER OF SEQ ID NOS: 6

<210> SEQ ID NO 1
<211> LENGTH: 5
<212> TYPE: PRT

```
<213> ORGANISM: Artificial Sequence
<220> FEATURE:
<223> OTHER INFORMATION: SYNTHETIC OLIGOPEPTIDE

<400> SEQUENCE: 1

Pro Thr Pro Leu Leu
1               5

<210> SEQ ID NO 2
<211> LENGTH: 5
<212> TYPE: PRT
<213> ORGANISM: Artificial Sequence
<220> FEATURE:
<223> OTHER INFORMATION: SYNTHETIC OLIGOPEPTIDE
<220> FEATURE:
<221> NAME/KEY: MOD_RES
<222> LOCATION: (5)..(5)
<223> OTHER INFORMATION: AMIDATION

<400> SEQUENCE: 2

Pro Thr Pro Leu Leu
1               5

<210> SEQ ID NO 3
<211> LENGTH: 5
<212> TYPE: PRT
<213> ORGANISM: Artificial Sequence
<220> FEATURE:
<223> OTHER INFORMATION: SYNTHETIC OLIGOPEPTIDE

<400> SEQUENCE: 3

Pro Pro Thr Leu Leu
1               5

<210> SEQ ID NO 4
<211> LENGTH: 6
<212> TYPE: PRT
<213> ORGANISM: Artificial Sequence
<220> FEATURE:
<223> OTHER INFORMATION: SYNTHETIC OLIGOPEPTIDE

<400> SEQUENCE: 4

Leu Ala Cys His Leu Leu
1               5

<210> SEQ ID NO 5
<211> LENGTH: 6
<212> TYPE: PRT
<213> ORGANISM: Artificial Sequence
<220> FEATURE:
<223> OTHER INFORMATION: SYNTHETIC OLIGOPEPTIDE

<400> SEQUENCE: 5

Glu Glu Leu Leu Pro Glu
1               5

<210> SEQ ID NO 6
<211> LENGTH: 6
<212> TYPE: PRT
<213> ORGANISM: Artificial Sequence
<220> FEATURE:
<223> OTHER INFORMATION: SYNTHETIC OLIGOPEPTIDE

<400> SEQUENCE: 6

His Ser Leu Leu Val Pro
1               5
```

PEPTIDES AND THEIR USE IN FOOD AND BEVERAGE

SEQUENCE LISTING

The present application contains a Sequence Listing which has been submitted via EFS-Web and is hereby incorporated by reference in its entirety. The ASCII copy of the Sequence Listing is named JMS_26416-06656_ST25.txt.

FIELD OF THE INVENTION

The present invention is related to a class of novel peptides and their use in food and beverage; more particularly, the present invention is related to novel peptides comprising a Leu-Leu moiety and their use in food and beverage such as coffee.

BACKGROUND OF THE INVENTION

The human body cannot synthesize certain amino acids that are necessary for health and growth, and instead must obtain them from food and beverage. These amino acids are called the "essential amino acids", and include Histidine, Isoleucine, Leucine (Leu), Lysine, Methionine, Phenylalanine, Threonine, Tryptophan, and Valine.

Traditionally, desirable mixtures of amino acids, such as mixtures comprising the essential amino acids, have been provided by hydrolyzing a protein with relatively high levels of essential amino acids, such as whey protein, or by combining free amino acids in a mixture that, optionally, may also include a hydrolyzed protein such as whey. However, the taste of such mixtures is very difficult to predict or to control; and they may be deemed unsuitable or undesirable for certain uses. As a result, flavoring agents sometimes have to be included into such mixtures to mask the taste of the free amino acids and/or hydrolyzed protein.

In some cases, compositions where a proportion of the amino acid content is provided by polypeptides or proteins are found to taste better than compositions where a higher proportion of total amino acids is provided as free amino acids or as certain hydrolyzed proteins. The availability of such polypeptide based or protein based compositions has been limited, however, because nutritional formulations have traditionally been made from protein which is isolated from natural food products, such as whey isolated from milk or soy protein isolated from soy. The amino acid profiles of those proteins do not necessarily meet the amino acid requirements for a mammal.

Advantageously, the present invention provides a class of novel peptides comprising a Leu-Leu moiety and their use in food and beverage such as coffee. The present invention exhibits numerous merits over the prior art. For example, the peptides provide at least some essential amino acids (e.g. Leucine); and the peptides improve the taste profile of foods and beverages, such as for example coffee, when added therein.

BRIEF DESCRIPTION OF THE INVENTION

One aspect of the present invention provides a peptide having an amino acid sequence according to formula (I):

$$Ax\text{-}Leu\text{-}Leu\text{-}Cy \quad (I)$$

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein the carboxylic acid group in the C-terminus of the peptide is optionally modified as an amide group; and
wherein x and y are integers, $x \geq 0$, $y \geq 0$, $2 \leq (x+y) \leq 15$.

Another aspect of the present invention provides a peptide composition comprising two or more different peptides, each of which has an amino acid sequence according to formula (I):

$$Ax\text{-}Leu\text{-}Leu\text{-}Cy \quad (I)$$

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein the carboxylic acid group in the C-terminus of the peptide is optionally modified as an amide group; and
wherein x and y are integers, $x \geq 0$, $y \geq 0$, $2 \leq (x+y) \leq 15$.

Still another aspect of the present invention provides a food or beverage product, such as for example coffee, comprising a peptide having an amino acid sequence according to formula (I):

$$Ax\text{-}Leu\text{-}Leu\text{-}Cy \quad (I)$$

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein the carboxylic acid group in the C-terminus of the peptide is optionally modified as an amide group; and
wherein x and y are integers, $x \geq 0$, $y \geq 0$, $2 \leq (x+y) \leq 15$.

A further aspect of the present invention provides a food or beverage product, such as for example coffee, comprising two or more different peptides, each of which has an amino acid sequence according to formula (I):

$$Ax\text{-}Leu\text{-}Leu\text{-}Cy \quad (I)$$

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein the carboxylic acid group in the C-terminus of the peptide is optionally modified as an amide group; and
wherein x and y are integers, $x \geq 0$, $y \geq 0$, $2 \leq (x+y) \leq 15$.

DETAILED DESCRIPTION OF THE INVENTION

Unless otherwise indicated, the following amino acids are represented by the following abbreviations. Alanine: Ala or A; Arginine: Arg or R; Asparagine: Asn or N; Aspartic acid:

Asp or D; Cysteine: Cys or C; Glutamic acid: Glu or E; Glutamine: Gln or Q; Glycine: Gly or G; Histidine: His or H; Isoleucine: Ile or I; Leucine: Leu or L; Lysine: Lys or K; Methionine: Met or M; Phenylalanine: Phe or F; Proline: Pro or P; Serine: Ser or S; Threonine: Thr or T; Tryptophan: Trp or W; Tyrosine: Tyr or Y; and Valine: Val or V.

When the carboxylic acid group in the C-terminus of the peptide is modified as an amide group, the peptide will be expressed as Ax-Leu-Leu-Cy-NH$_2$.

The amino acids of the peptide can be Dextro- (D-) and/or Levo- (L-) α-amino acids, β-amino acids as well as other organic compounds containing at least one primary and/or secondary amino group and at least one carboxylic acid group. Preferably, the amino acids are α-amino acids, even more preferably L-α-amino acids, whereby proteinogenic amino acids are particularly preferred.

Unless otherwise indicated, an amino acid sequence also includes its substitutions. Substitutions preferably may be conservative or highly conservative. A conservative substitution refers to the substitution of an amino acid with another that has generally the same net electronic charge and generally the same size and shape. For instance, amino acids with aliphatic or substituted aliphatic amino acid side chains have approximately the same size when the total number of carbon and heteroatoms in their side chains differs by no more than about four. They have approximately the same shape when the number of branches in their side chains differs by no more than about one or two. Amino acids with phenyl or substituted phenyl groups in their side chains are considered to have about the same size and shape. Listed below are five groups of amino acids. Replacing an amino acid in a compound with another amino acid from the same groups generally results in a conservative substitution.

Group I: glycine, alanine, valine, leucine, isoleucine, serine, threonine, cysteine, methionine and non-naturally occurring amino acids with $C_1$-$C_4$ aliphatic or $C_1$-$C_4$ hydroxyl substituted aliphatic side chains (straight chained or monobranched). Group II: glutamic acid, aspartic acid and non-naturally occurring amino acids with carboxylic acid substituted $C_1$-$C_4$ aliphatic side chains (unbranched or one branch point). Group III: lysine, ornithine, arginine and non-naturally occurring amino acids with amine or guanidino substituted $C_1$-$C_4$ aliphatic side chains (unbranched or one branch point). Group IV: glutamine, asparagine and non-naturally occurring amino acids with amide substituted $C_1$-$C_4$ aliphatic side chains (unbranched or one branch point). Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine.

Salts of the described peptides that are useful in foods and beverages include acid addition salts, metal salts, organic base addition salts and the like. The acid addition salts include inorganic acid salts such as hydrochloride, sulfate, phosphate and the like, and organic acid salts such as acetate, malate, fumarate, tartarate, citrate and the like. The metal salts include alkali metal salts such as sodium salts, potassium salts, etc.; alkaline earth metal salts such as magnesium salts, calcium salts, etc.; aluminum salts, zinc salts and the like. The organic base addition salts include salts formed with a primary amine such as methylamine, ethylamine, aniline, etc., a secondary amine such as dimethylamine, diethylamine, pyrrolidine, piperidine, morpholine, piperazine, etc.; or a tertiary amine such as trimethylamine, triethylamine, N,N-dimethylaniline, pyridine, etc.; ammonium salts; and the like.

Various exemplary embodiments of the described peptides include, but are not limited to, the following.

Embodiment #1

A peptide having an amino acid sequence according to formula (I):

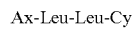
    Ax-Leu-Leu-Cy           (I)

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;

wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;

wherein the carboxylic acid group in the C-terminus of the peptide is optionally modified as an amide group; and wherein x and y are integers, x≥0, y≥0, 2≤(x+y)≤15.

For example, Ax-Leu-Leu-Cy may mean that the C-terminus of the peptide is a carboxylic acid, and Ax-Leu-Leu-Cy-NH$_2$ may mean that the C-terminus of the peptide is an amide.

Embodiment #2

The peptide according to Embodiment #1, wherein said x amino acid residues are independently of each other selected from Tyr, Phe, Asn, Leu, Pro, Thr, Ala, Cys, His, Glu, Ser, and Val.

Embodiment #3

The peptide according to Embodiment #1, wherein said y amino acid residues are independently of each other selected from Tyr, Phe, Asn, Leu, Pro, Thr, Ala, Cys, His, Glu, Ser, and Val.

Embodiment #4

The peptide according to Embodiment #1, wherein said x amino acid residues and y amino acid residues are independently of each other selected from Tyr, Phe, Asn, Leu, Pro, Thr, Ala, Cys, His, Glu, Ser, and Val.

Embodiment #5

The peptide according to Embodiment #1, wherein said x amino acid residues are independently of each other selected from Tyr, Phe, Asn, Pro, Thr, Leu, Ala, Cys, His, Glu, and Ser.

Embodiment #6

The peptide according to Embodiment #1, wherein said y amino acid residues are independently of each other selected from Pro, Glu, and Val.

Embodiment #7

The peptide according to Embodiment #1, wherein said x amino acid residues are independently of each other selected from Tyr, Phe, Asn, Pro, Thr, Leu, Ala, Cys, His, Glu, and Ser; and said y amino acid residues are independently of each other selected from Pro, Glu, and Val.

Embodiment #8

The peptide according to Embodiment #1, wherein $3 \leq (x+y) \leq 10$.

Embodiment #9

The peptide according to Embodiment #1, wherein $3 \leq (x+y) \leq 6$.

Embodiment #10

The peptide according to Embodiment #1, wherein $3 \leq (x+y) \leq 4$.

Embodiment #11

The peptide according to Embodiment #1, wherein $2 \leq x \leq 4$.

Embodiment #12

The peptide according to Embodiment #1, wherein $0 \leq y \leq 2$.

Embodiment #13

The peptide according to Embodiment #1, wherein $2 \leq x \leq 4$, and $0 \leq y \leq 2$.

Embodiment #14

The peptide according to Embodiment #1, wherein Ax represents an amino acid sequence selected from Glu-Glu; His-Ser; Pro-Thr-Pro; Pro-Pro-Thr; and Leu-Ala-Cys-His.

Embodiment #15

The peptide according to Embodiment #1, wherein Cy represents an amino acid sequence selected from Pro-Glu; and Val-Pro.

Embodiment #16

The peptide according to Embodiment #1, wherein Ax represents an amino acid sequence selected from Glu-Glu; His-Ser; Pro-Thr-Pro; Pro-Pro-Thr; and Leu-Ala-Cys-His; and wherein Cy represents an amino acid sequence selected from Pro-Glu; and Val-Pro.

Embodiment #17

The peptide according to Embodiment #1, wherein said amino acid sequence according to formula (I) is selected from:
SEQ ID NO: 1 Pro-Thr-Pro-Leu-Leu,
SEQ ID NO: 2 Pro-Thr-Pro-Leu-Leu-NH$_2$,
SEQ ID NO: 3 Pro-Pro-Thr-Leu-Leu,
SEQ ID NO: 4 Leu-Ala-Cys-His-Leu-Leu,
SEQ ID NO: 5 Glu-Glu-Leu-Leu-Pro-Glu, and
SEQ ID NO: 6 His-Ser-Leu-Leu-Val-Pro.

Various exemplary embodiments of the described peptide compositions include, but are not limited to, the following.

Embodiment #18

A peptide composition comprising two or more different peptides, each of which has an amino acid sequence according to formula (I):

$$Ax\text{-}Leu\text{-}Leu\text{-}Cy \qquad (I)$$

wherein Ax represents an amino acid sequence including x amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein Cy represents an amino acid sequence including y amino acid residues, which are independently of each other selected from Ala, Arg, Asn, Asp, Cys, Glu, Gln, Gly, His, Ile, Leu, Lys, Met, Phe, Pro, Ser, Thr, Trp, Tyr, and Val;
wherein the carboxylic acid group in the C-terminus of the peptide is optionally modified as an amide group; and
wherein x and y are integers, $x \geq 0$, $y \geq 0$, $2 \leq (x+y) \leq 15$.

Embodiment #19

The peptide composition according to Embodiment #18, wherein said x amino acid residues are independently of each other selected from Tyr, Phe, Asn, Leu, Pro, Thr, Ala, Cys, His, Glu, Ser, and Val.

Embodiment #20

The peptide composition according to Embodiment #18, wherein said y amino acid residues are independently of each other selected from Tyr, Phe, Asn, Leu, Pro, Thr, Ala, Cys, His, Glu, Ser, and Val.

Embodiment #21

The peptide composition according to Embodiment #18, wherein said x amino acid residues and y amino acid residues are independently of each other selected from Tyr, Phe, Asn, Leu, Pro, Thr, Ala, Cys, His, Glu, Ser, and Val.

Embodiment #22

The peptide composition according to Embodiment #18, wherein said x amino acid residues are independently of each other selected from Tyr, Phe, Asn, Pro, Thr, Leu, Ala, Cys, His, Glu, and Ser.

Embodiment #23

The peptide composition according to Embodiment #18, wherein said y amino acid residues are independently of each other selected from Pro, Glu, and Val.

Embodiment #24

The peptide composition according to Embodiment #18, wherein said x amino acid residues are independently of each other selected from Tyr, Phe, Asn, Pro, Thr, Leu, Ala, Cys, His, Glu, and Ser; and said y amino acid residues are independently of each other selected from Pro, Glu, and Val.

Embodiment #25

The peptide composition according to Embodiment #18, wherein 3≤(x+y)≤10.

Embodiment #26

The peptide composition according to Embodiment #18, wherein 3≤(x+y)≤6.

Embodiment #27

The peptide composition according to Embodiment #18, wherein 3≤(x+y)≤4.

Embodiment #28

The peptide composition according to Embodiment #18, wherein 2≤x≤4.

Embodiment #29

The peptide composition according to Embodiment #18, wherein 0≤y≤2.

Embodiment #30

The peptide composition according to Embodiment #18, wherein 2≤x≤4, and 0≤y≤2.

Embodiment #31

The peptide composition according to Embodiment #18, wherein Ax represents an amino acid sequence selected from Glu-Glu; His-Ser; Pro-Thr-Pro; Pro-Pro-Thr; and Leu-Ala-Cys-His.

Embodiment #32

The peptide composition according to Embodiment #18, wherein Cy represents an amino acid sequence selected from Pro-Glu; and Val-Pro.

Embodiment #33

The peptide composition according to Embodiment #18, wherein Ax represents an amino acid sequence selected from Glu-Glu; His-Ser; Pro-Thr-Pro; Pro-Pro-Thr; and Leu-Ala-Cys-His; and wherein Cy represents an amino acid sequence selected from Pro-Glu; and Val-Pro.

Embodiment #34

The peptide composition according to Embodiment #18, wherein said two or more different peptides are selected from Pro-Thr-Pro-Leu-Leu, Pro-Thr-Pro-Leu-Leu-NH$_2$, Pro-Pro-Thr-Leu-Leu, Leu-Ala-Cys-His-Leu-Leu, Glu-Glu-Leu-Leu-Pro-Glu, and His-Ser-Leu-Leu-Val-Pro.

Embodiment #35

The peptide composition according to Embodiment #18, which comprises Pro-Pro-Thr-Leu-Leu, Glu-Glu-Leu-Leu-Pro-Glu, and His-Ser-Leu-Leu-Val-Pro.

Embodiment #36

The peptide composition according to Embodiment #35, wherein the weight ratio between Pro-Pro-Thr-Leu-Leu, Glu-Glu-Leu-Leu-Pro-Glu, and His-Ser-Leu-Leu-Val-Pro is represented by 1:m:n, wherein 0.5≤m≤2, and 0.5≤n≤2.

Embodiment #37

The peptide composition according to Embodiment #35, wherein 0.8≤m≤1.5, and 0.9≤n≤1.1.

Embodiment #38

The peptide composition according to Embodiment #35, wherein 0.9≤m≤1.1, and 0.95≤n≤1.05.

Embodiment #39

The peptide composition according to Embodiment #35, wherein m=1, and n=1.

Embodiment #40

The peptide composition according to Embodiment #18, which comprises Pro-Thr-Pro-Leu-Leu, Pro-Thr-Pro-Leu-Leu-NH$_2$, Pro-Pro-Thr-Leu-Leu, Leu-Ala-Cys-His-Leu-Leu, Glu-Glu-Leu-Leu-Pro-Glu, and His-Ser-Leu-Leu-Val-Pro.

Embodiment #41

The peptide composition according to Embodiment #40, wherein the weight ratio between Pro-Thr-Pro-Leu-Leu, Pro-Thr-Pro-Leu-Leu-NH$_2$, Pro-Pro-Thr-Leu-Leu, Leu-Ala-Cys-His-Leu-Leu, Glu-Glu-Leu-Leu-Pro-Glu, and His-Ser-Leu-Leu-Val-Pro is represented by 1:p:q:r:s:t, wherein 0.8≤p≤1.2, 0.8≤q≤1.2, 0.8≤r≤1.2, 0.8≤s≤1.2, and 0.8≤t≤1.2.

Embodiment #42

The peptide composition according to Embodiment #41, wherein 0.9≤p≤1.1, 0.9≤q≤1.1, 0.9≤r≤1.1, 0.9≤s≤1.1, and 0.9≤t≤1.1.

Embodiment #43

The peptide composition according to Embodiment #41, wherein 0.99≤p≤1.05, 0.95≤q≤1.05, 0.95≤r≤1.05, 0.95≤s≤1.05, and 0.95≤t≤1.05.

Embodiment #44

The peptide composition according to Embodiment #41, wherein p=1, q=1, r=1, s=1, and t=1.

Various exemplary embodiments of the food or beverage product comprising the described peptide or peptide composition include, but are not limited to, the following.

Embodiment #45

A food or beverage product comprising the peptide of Embodiment #1.

Embodiment #46

A food or beverage product comprising the peptide composition of Embodiment #18.

Embodiment #47

The food/beverage product according to Embodiment #45 or Embodiment #46, which is selected from juices and soups.

Embodiment #48

The food/beverage product according to Embodiment #45 or Embodiment #46, which is selected from confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarised gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, breakfast cereals, ready-to-eat (rte) cereals, family breakfast cereals, flakes, muesli, other rte cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavoured fromage frais and quark, savoury fromage frais and quark, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, ultra heat treatment (uht) soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and pures, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Embodiment #49

The food/beverage product according to Embodiment #45 or Embodiment #46, which is selected from dehydrated and freeze dried soups, including dehydrated soup mixes, dehydrated instant soups, dehydrated ready-to-cook soups, dehydrated or ambient preparations of ready-made dishes, meals and single serve entrees including pasta, and potato and rice dishes.

Embodiment #50

The food/beverage product according to Embodiment #45 or Embodiment #46, which is selected from condiments, marinades, salad dressings, salad toppings, dips, breading, batter mixes, shelf stable spreads, barbecue sauces, liquid recipe mixes, concentrates, sauces or sauce mixes.

Embodiment #51

The food/beverage product according to Embodiment #45 or Embodiment #46, which is selected from alcoholic and non-alcoholic ready to drink and dry powdered beverages.

Embodiment #52

The food/beverage product according to Embodiment #45 or Embodiment #46, which is selected from carbonated and non-carbonated beverages, e.g., sodas, fruit or vegetable juices.

Embodiment #53

The food/beverage product according to Embodiment #45 or Embodiment #46, which is selected from tea, roast and ground coffee, coffee brew, and coffee creamer.

Embodiment #54

The food/beverage product according to Embodiment #45 or Embodiment #46, which is selected from instant coffee, liquid coffee concentrate, and decaf coffee.

Embodiment #55

The food/beverage product according to Embodiment #45 or Embodiment #46, which is coffee brew made from instant coffee, liquid coffee concentrate, or decaf coffee.

Embodiment #56

The food/beverage product according to Embodiment #55, wherein the total amount of the peptide(s) in the coffee brew is in the range of from about 4 ppm to about 40 ppm by weight.

The described peptides can be prepared by suitable chemical synthesis methods, e.g. the azide method, the acid chloride method, the acid anhydride method, the mixed acid anhydride method, the N,N'-Dicyclohexylcarbodiimide (DCC) method, the active ester method, the carboimidazol method, the oxidation-reduction method, and the DCC-active method. Known methods may be utilized to prepare a peptide wherein the carboxylic acid group in the C-terminus is replaced with an amide group. These peptide synthesis methods include solid phase synthesis, liquid phase synthesis (AKA solution phase synthesis), as well as hybrid solid and liquid phase peptide synthesis. Processes for extraction of peptides are generally employed in various types of chemical peptide synthesis.

Alternatively, the peptides of the present invention can be prepared by suitable biotechnical methods. For example, according to the amino acid sequences, peptides can also be prepared by cloning the nucleotide sequences corresponding to the amino acid sequences of the peptides into suitable vectors and expressed in suitable host cells, plants or animals.

The peptides of the present invention can also be obtained commercially from companies specialized in peptide synthesis, for example, EZBiolab Inc. located at 1033 3$^{rd}$ Avenue SW, Carmel, Ind. 46032, USA.

Solid Phase Peptide Synthesis (SPPS)

Commonly used abbreviations in this SPPS section include: acetyl (Ac), azo-bis-isobutyrylnitrile (AIBN), atmospheres (Atm), 9-borabicyclo[3.3.1]nonane (9-BBN), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), (3-(Diethoxyphosphoryloxy)-1,2,3-benzotriazin-4(3H)-one) (DEPBT), di-iso-propylazodicarboxylate (DIAD), di-iso-butylaluminumhydride (DIBAL), di-iso-propylethylamine (DIPEA), N,N-dimethyl acetamide (DMA), 4-N,N-dimethylaminopyridine (DMAP), ethylene glycol dimethyl ether (DME), N,N-dimethylformamide (DMF), dimethyl sulfoxide (DMSO), 1,1'-bis-(diphenylphosphino)ethane (dppe), 1,1'-bis-(diphenylphosphino) ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), MeSO$_2$-(mesyl), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), (benzotriazol-1-yloxy)tripyrrolidinophosphonium hexafluorophosphate (PyBOP), room temperature (RT), tert-butyldimethylsilyl or t-BuMe$_2$Si (TBDMS), triethylamine (TEA), 2,2,6,6-tetramethylpiperidine 1-oxyl (TEMPO), triflate or CF$_3$SO$_2$-(Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TSOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety.

In solid phase peptide synthesis (SPPS), an amino acid or peptide group is typically bound to a solid support. Then, successive amino acids or peptide groups are attached to the support-bound peptide until the peptide material of interest is formed. The support-bound peptide is then cleaved from the support and subject to further processing and/or purification. In some cases, solid phase synthesis yields a mature peptide product; in other cases the peptide cleaved from the support (i.e., a "peptide intermediate fragment") is used in the preparation of a larger, mature peptide product.

Any type of support suitable in the practice of solid phase peptide synthesis can be used. In preferred embodiments, the support comprises a resin that can be made from one or more polymers, copolymers or combinations of polymers such as polyamide, polysulfamide, substituted polyethylenes, polyethyleneglycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can have linkers that are photo-cleavable, TFA-cleavable, HF-cleavable, fluoride ion-cleavable, reductively-cleavable; Pd(O)-cleavable; nucleophilically-cleavable; or radically-cleavable. Preferred linking moieties are cleavable under conditions such that the side-chain groups of the cleaved peptide are still substantially globally protected.

In one preferred method of synthesis, the peptide intermediate fragments synthesized on an acid sensitive solid support that includes trityl groups, and more preferably on a resin that includes trityl groups having pendent chlorine groups, for example a 2-chlorotrityl chloride (2-CTC) resin. Examples also include trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin.

Some preferred solid supports include polystyrene, which can be copolymerized with divinylbenzene, to form support material to which the reactive groups are anchored.

Other resins that are used in solid phase synthesis include "Wang" resins, which comprise a copolymer of styrene and divinylbenzene with 4-hydroxymethylphenyloxymethyl anchoring groups, and 4-hydroxymethyl-3-methoxyphenoxybutyric acid resin. The Wang, 2-chlorotrityl chloride, and 4-hydroxymethyl-3-methoxyphenoxy butyric acid resins can be purchased from, for example, Calbiochem-Novabiochem Corp., San Diego, Calif.

In order to prepare a resin for solid phase synthesis, the resin can be pre-washed in suitable solvent(s). For example, a solid phase resin such as a 2-CTC resin is added to a peptide chamber and pre-washed with a suitable solvent. The pre-wash solvent may be chosen based on the type of solvent (or mixture of solvents) that is used in the coupling reaction, or vice versa. Solvents that are suitable for washing, and also the subsequent coupling reaction include dichloromethane (DCM), dichloroethane (DCE), dimethylformamide (DMF), and the like, as well as mixtures of these reagents. Other useful solvents include DMSO, pyridine, chloroform, dioxane, tetrahydrofuran, ethyl acetate, N-methylpyrrolidone, and mixtures thereof. In some cases coupling can be performed in a binary solvent system, such as a mixture of DMF and DCM at a volume ratio in the range of 9:1 to 1:9, more commonly 4:1 to 1:4.

The SPPS syntheses preferably are carried out in the presence of appropriate protecting groups unless otherwise noted. The nature and use of protecting groups is well known in the art. Generally, a suitable protecting group is any sort of group that that can help prevent the atom or moiety to which it is attached, e.g., oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols and the like.

A side chain protecting group refers to a chemical moiety coupled to the side chain (i.e., R group in the general amino acid formula $H_2N-C(R)(H)-COOH$ of an amino acid that helps to prevent a portion of the side chain from reacting with chemicals used in steps of peptide synthesis, processing, etc. The choice of a side chain-protecting group can depend on various factors, for example, type of synthesis performed, processing to which the peptide will be subjected, and the desired intermediate product or final product. The nature of the side chain protecting group also depends on the nature of the amino acid itself. Generally, a side chain protecting group is chosen that is not removed during deprotection of the α-amino groups during the solid phase synthesis. Therefore the α-amino protecting group and the side chain protecting group are typically not the same.

In some cases, and depending on the type of reagents used in solid phase synthesis and other peptide processing, an amino acid may not require the presence of a side-chain protecting group. Such amino acids typically do not include a reactive oxygen, nitrogen, or other reactive moiety in the side chain.

Examples of side chain protecting groups include acetyl (Ac), benzoyl (Bz), tert-butyl, triphenylmethyl (trityl), tetrahydropyranyl, benzyl ether (Bzl) and 2,6-dichlorobenzyl (DCB), t-butoxycarbonyl (Boc), nitro, p-toluenesulfonyl (Tos), adamantyloxycarbonyl, xanthyl (Xan), benzyl, 2,6-dichlorobenzyl, methyl, ethyl and t-butyl ester, benzyloxycarbonyl (cBz or Z), 2-chlorobenzyloxycarbonyl (2-Cl—Z), t-amyloxycarbonyl(Aoc), and aromatic or aliphatic urethan-type protecting groups. photolabile groups such as nitroveratryloxycarbonyl (NVOC); and fluoride labile groups such as 2-trimethylsilylethoxycarbonyl (TEOC).

An amino-terminal protecting group includes a chemical moiety coupled to the alpha amino group of an amino acid. Typically, the amino-terminal protecting group is removed in a deprotection reaction prior to the addition of the next amino acid to be added to the growing peptide chain, but can be maintained when the peptide is cleaved from the support. The choice of an amino terminal protecting group can depend on various factors, for example, type of synthesis performed and the desired intermediate product or final product.

Examples of amino-terminal protecting groups include (1) acyl-type protecting groups, such as formyl, acrylyl (Acr), benzoyl (Bz) and acetyl (Ac); (2) aromatic urethane-type protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (Boc), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenyl-methyloxycarbonyl (Fmoc), 2-(4-biphenylyl)-propyl(2)oxycarbonyl (Bpoc), 2-phenylpropyl(2)-oxycarbonyl (Poc) and t-butyloxycarbonyl (Boc).

Fmoc or Fmoc-like chemistry is highly preferred for solid phase peptide synthesis, inasmuch as cleaving the resultant peptide in a protected state is relatively straightforward to carry out using mildly acidic cleaving agents. This kind of cleaving reaction is relatively clean in terms of resultant by-products, impurities, etc., making it technically and economically feasible to recover peptide on a large scale basis from both the swelling and shrinking washes, enhancing yield. As used herein, "large scale" with respect to peptide synthesis generally includes the synthesis of peptides in the range of at least 500 g, more preferably at least 2 kg per batch. Large-scale synthesis is typically performed in large reaction vessels, such as steel reaction vessels, that can accommodate quantities of reagents such as resins, solvents, amino acids, chemicals for coupling, and deprotection reactions, that are sized to allow for production of peptides in the kilogram to metric ton range.

Additionally, the Fmoc protecting group can be selectively cleaved from a peptide relative to the side chain protecting groups so that the side chain protection are left in place when the Fmoc is cleaved. This kind of selectivity is important during amino acid coupling to minimize side chain reactions. Additionally, the side chain protecting groups can be selectively cleaved to remove them relative to the Fmoc, leaving the Fmoc in place. This latter selectivity is very advantageously relied upon during purification schemes described further below.

The solid phase coupling reaction can be performed in the presence of one or more compounds that enhance or improve the coupling reaction. Compounds that can increase the rate of reaction and reduce the rate of side reactions include phosphonium and uronium salts that can, in the presence of a tertiary base, for example, diisopropylethylamine (DIEA) and triethylamine (TEA), convert protected amino acids into activated species (for example, BOP, PyBOP, HBTU, and TBTU, which generate HOBt esters, and DEPBT which generates an HOOBt ester). Other reagents help prevent racemization by providing a protecting reagent. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu). The mixed anhydride method, using isobutyl chloroformate, with or without an added auxiliary nucleophile, may also be utilized, as can the azide method, due to the low racemization associated with it. These types of compounds can also increase the rate of carbodiimide-mediated couplings, as well as prevent dehydration of Asn and Gln residues.

After the coupling is determined to be complete, the coupling reaction mixture is washed with a solvent, and the coupling cycle is repeated for each of the subsequent amino acid residues of the peptide material. In order to couple the next amino acid, removal of the N-terminal protecting group (for example, an Fmoc group) from the resin-bound material is typically accomplished by treatment with a reagent that includes 20-50% (on a weight basis) piperidine in a solvent, such as N-methylpyrrolidone (NMP) or dimethylformamide (DMF). After removal of the Fmoc protecting group, several washes are typically performed to remove residual piperidine and Fmoc by-products (such as dibenzofulvene and its piperidine adduct).

The subsequent amino acids can be utilized at a stoichiometric excess of amino acids in relation to the loading factor of peptide material on the resin support. Generally, the amount of amino acids used in the coupling step is at least equivalent to the loading factor of the first amino acid on the resin (1 equivalent or more). Preferably the amount of amino acids used in the coupling step is at least 1.3 equivalent (0.3 excess) or more, and most preferably about 1.5 equivalent (0.5 excess) or more. In some cases, for example, the coupling step utilizes an amount equivalent of amino acids in the range between 1 and 3.

Following the final coupling cycle, the resin is washed with a solvent such as NMP, and then washed with an inert second solvent such as DCM. In order to remove the synthesized peptide material from the resin, a cleaving treatment is carried out in a manner such that the cleaved peptide material still bears sufficient side chain and terminus protecting groups. Leaving the protective groups in place helps to prevent undesirable coupling or other undesirable reactions of peptide fragments during or after resin cleavage. In the case when Fmoc or similar chemistry is used to synthesize the peptide, protected cleavage may be accomplished in any desired fashion such as by using a relatively weak acid reagent such as acetic acid or dilute TFA in a solvent such as DCM. The use of 0.5 to 10 weight percent, preferably 1 to 3 weight percent TFA in DCM is typical.

Steps of cleaving the peptide intermediate fragment from the solid phase resin can proceed along the lines of an exemplary process as follows. However, any suitable process that effectively cleaves the peptide intermediate fragment from the resin can be used. For example, approximately 5 to 20, preferably about 10 volumes of a solvent containing an acidic cleaving reagent is added to the vessel containing the resin-bound peptide material. The resin, typically in the form of beads, is immersed in the reagent as a consequence. The cleaving reaction occurs as the liquid contents are agitated at a suitable temperature for a suitable time period. Agitation helps prevent the beads from clumping. Suitable time and temperature conditions will depend upon factors such as the acid reagent being used, the nature of the peptide, the nature of the resin, and the like. As general guidelines, stirring at from about −15° C. to about 5° C., preferably from about −10° C. to about 0° C. for about 5 minutes to two hours, preferably about 25 minutes to about 45 minutes would be suitable. Cleaving time may be in the range of from about 10 minutes to about 2 hours or even as much as a day. Cleaving is desirably carried out in such a chilled temperature range to accommodate a reaction exotherm that might typically occur during the reaction. In addition, the lower temperature of the cleavage reaction prevents acid sensitive side chain protecting groups, such as trt groups, from being removed at this stage.

At the end of the cleaving treatment, the reaction is quenched. This may be achieved, for example, by combining the cleaving reagent with a suitable base, such as pyridine or the like, and continuing to agitate and stir for an additional period such as for an additional 5 minutes to 2 hours, preferably about 20 minutes to about 40 minutes. Adding the base and continued agitation causes the temperature of the vessel contents to increase. At the end of agitation, the vessel contents may be at a temperature in the range of from about 0° C. to about 15° C., preferably about 5° C. to about 10° C. Factors such as swelling and shrinking the resin in order to improve aspects of the peptide recovery can optionally be incorporated into the overall synthesis process.

In some aspects, the cleaved peptide fragments can be prepared for liquid phase coupling to other peptide fragments and/or amino acids. Liquid phase synthesis can be particularly useful in cases where the synthesis of a useful mature peptide is not achievable by solid phase. For example, in solid phase synthesis, longer peptides eventually may adopt an irregular conformation while still attached to the solid support, making it difficult to add additional amino acids or peptide material to the growing chain. As the peptide chain becomes longer on the support resin, the efficiency of process steps such as coupling and deprotection may be compromised. This, in turn, can result in longer processing times to compensate for these problems, in addition to incremental losses in starting materials, such as activatable amino acids, co-reagents, and solvents. These problems can increase as the length of the peptide increases.

Therefore, it is relatively uncommon to find mature peptides of greater than 30 amino acids in length synthesized in a single fragment using solid phase procedures alone. Instead, individual fragments may be separately synthesized on the solid phase, and then coupled in the solid and/or solution phase to build the desired peptide product. LPPS is particularly often used for industrial large-scale preparations of peptides.

Coupling of peptide intermediate fragments to other fragments or amino acid(s) in the liquid phase can be carried out using in situ coupling reagents, for example benzotriazol-1-yl-oxy-tris-(dimethylamino)phosphoniumhexafluorophosphate (BOP), benzotriazol-1-yl-oxy-tripyrrolidinophosphonium hexafluorophosphate (PyBOP), o-(benzotriazol-1-yl)-N,N,N',N'-tetramethyluronium hexafluorophosphate (HBTU), o-(7-azabenzotriazol-1-yl)-1,1,3,3-tetramethyluronium hexafluoroborate (HATU), o-(7-azabenzotriazol-1-yl)-1,1,3,3-tetramethyluronium tetrafluorophosphate (TATU), o-(1H-6-chloro-benzotriazol-1-yl)-1,1,3,3-tetramethyluronium hexafluorophosphate (HCTU), o-(1H-6-chloro-benzotriazol-1-yl)-1,1,3,3-tetramethyluronium tetrafluoroborate (TCTU), o-(benzotriazol-1-yl)oxybios-(pyrrolidino)-uronium hexafluorophosphate (HAPyU), dicyclohexylcarbodiimide (DCC), diisopropylcarbodiimide, 3-(diethoxyphosphoryloxy)-1,2,3-benzotriazine-4(3H)-one (DEPBT), water-soluble carbodiimide (WSCDI), o-(cyano-ethoxycarbonyl-methyleneamino)-N,N,N',N''-tetramethyluronium tetrafluoroborate (TOTU) or o-(benzotriazol-1-yl)-N,N,N',N'-tetramethyluronium tetrafluoroborate (TBTU).

Other coupling techniques use preformed active esters such as hydroxysuccinimide (HOSu) and p-nitrophenol (HONP) esters; preformed symmetrical anhydrides; non-symmetrical anhydrides such as N-carboxyanhydrides (NCAs); or acid halides such as acyl fluoride as well as acyl chloride.

A suitable coupling solvent can be used in the solution phase coupling reaction. It is understood that the coupling solvent(s) can affect the degree of racemization of the peptide bond formed; the solubility of the peptide and/or peptide fragments; and the coupling reaction rate. In some embodiments, the coupling solvent includes one or more water-miscible reagents. Examples of water-miscible solvents include, for example, DMSO, pyridine, chloroform, dioxane, tetrahydrofuran, ethyl acetate, N-methylpyrrolidone, dimethylformamide, dioxane, or mixtures thereof.

In other embodiments, the coupling reaction may include one or more non water-miscible reagents. An exemplary non water-miscible solvent is methylene chloride. In these embodiments, the non water-miscible solvent is preferably compatible with the deprotection reaction; for example, if a non water-miscible solvent is used preferably it is selected so that it does not adversely affect the deprotection reaction.

After the target peptide is formed, the product can be subject to deprotection, purification, lyophilization, further processing (e.g., reaction with another peptide to form a fusion protein); combinations of these, and/or the like, as desired.

For example, according to the invention, the side-chain protecting groups are typically retained on the peptide intermediate fragments throughout solid phase synthesis and also into and throughout the liquid phase coupling reactions. Generally, after solution phase step is completed, one or more deprotection steps may be performed to remove one or more protecting groups from the peptide.

The removal of side chain protecting groups by global deprotection typically utilizes a deprotection solution that includes an acidolytic agent to cleave the side chain protecting groups. Commonly used acidolytic reagents for global deprotection include neat trifluoroacetic acid (TFA), HCl, Lewis acids such as $BF_3Et_2O$ or $Me_3SiBr$, liquid hydrofluoric acid (HF), hydrogen bromide (HBr), trifluoromethanesulfonic acid, and combinations thereof. The deprotection solution also includes one or more suitable cation scavengers, for example, dithiothreitol (DTT), anisole, p-cresol, ethanedithiol, or dimethyl sulfide. The deprotection solution can also include water. As used herein, amounts of reagents present in the deprotection composition are typically expressed in a ratio, wherein the amount of an individual component is expressed as a numerator in "parts", such as "parts weight" or "parts volume" and the denominator is the total parts in the composition. For example, a deprotection solution containing $TFA:H_2O:DTT$ in a ratio of 90:5:5 (weight/weight/weight) has TFA at 90/100 parts by weight, $H_2O$ at 5/100 parts by weight, and DTT at 5/100 parts by weight.

The precipitation may be done using an ether, e.g., diethyl ether or MTBE (Methyl Tert Butyl Ether). After precipitation, the peptide is isolated and dried before being combined with other ingredients, lyophilized, packaged, stored, further processed, and/or otherwise handled. This may be accomplished in any suitable fashion. In one approach, the peptide is collected via filtering, washed with ample MTBE washes to reduce final salt content to a suitable level, and then dried.

A preferred purification process involves at least two purification passes through chromatographic media, wherein at least a first pass occurs at a first pH and at least a second pass occurs at a second pH. More preferably, the first pass occurs at an acidic pH, while the second pass occurs at a basic pH. In various other embodiments, at least one pass under acidic conditions occurs prior to a pass occurring under basic conditions.

The pH values, whether acid or base, promote uniformity in that a uniform ionic species is present in each instance. Thus, the acidic pH desirably is sufficiently low so that substantially all of the amino acid residues in the peptide material are protonated. Desirably, the basic pH should be high enough so that substantially all of the amino acid residues in the peptide material are deprotonated. The acid and base chromatography can be carried out in any order. It is convenient to do the basic chromatography last when the peptide acetate is a desired product inasmuch as the acetate may be the product of chromatography.

Liquid Phase Peptide Synthesis (LPPS)

In this section, the following abbreviations have the meaning as given in the following list, if not otherwise stated: ACN acetonitrile; Boc tert-butoxycarbonyl; Bsmoc 1,1-dioxobenzo[b]thiophen-2-ylmethyloxycarbonyl; Bzl benzyl; Cbz benzyloxycarbonyl; DCC N,N'-dicyclohexylcarbodiimide; DCE dichloroethane; DCM dichloromethane; DCU N,N'-dicyclohexylurea; DEA diethylamine; DIPE diisopropyl ether; DIPEA N,N-diisopropylethylamine; DMA N,N-dimethylacetamide; DMF N,N-dimethylformamide; DOE design of experiments; EDC 1-ethyl-3-(3-dimethylaminopropyl)carbodiimide; eq equivalent(s); EtOAc ethylacetate; Fmoc fluorenyl-9-methoxycarbonyl; h hour(s); HOBt 1-hydroxybenzotriazole; $HOBt.H_2O$ 1-hydroxybenzotriazole monohydrate; HPLS high-performance liquid chromatography; LPPS liquid phase peptide synthesis; MeTHF 2-methyltetrahydrofuran; min minute(s); MS mass spectrometry; NMP N-methyl-2-pyrrolidone; OMe methoxy; OtBu tert-butoxy; PG protecting group; PyBOP benzotriazol-1-yloxy-tris(pyrrolidino)-phosphonium hexafluorophosphate; RM reaction mixture; SPPS solid phase peptide synthesis; TAEA tris(2-aminoethyl)amine; TBTU O-(benzotriazol-1-yl)-1,1,3,3-tetramethyluronium tetrafluoroborate; tBu tert-butyl; TEA triethylamine; TFA trifluoroacetic acid; THF tetrahydrofuran; TLC thin layer chromatography; TOTU O-[cyano(ethoxycarbonyl)methylenamino]-1,1,3,3-tetramethyluronium tetrafluoroborate; Trt trityl; and UV ultraviolet.

In liquid phase coupling, two peptide intermediate fragments, a peptide intermediate fragment and a reactive amino acid, or two reactive amino acids are coupled in an appropriate solvent, usually in the presence of additional reagents that promote the efficiency and quality of the coupling reaction. The peptide intermediate fragments are reactively arranged so the N-terminal of one fragment becomes coupled to the C-terminal of the other fragment, or vice versa. In addition, side chain protecting groups, which are present during solid phase synthesis, are commonly retained on the fragments during liquid phase coupling to ensure the specific reactivity of the terminal ends of the fragments. These side chain protecting groups are typically not removed until a mature peptide has been formed.

General LPPS involves coupling of two partially protected amino acids or peptides, whereby one of them bears an unprotected C-terminal carboxylic acid group and the other one bears an unprotected N-terminal amino group. After completion of the coupling step, the N-terminal amino group or, alternatively, the C-terminal carboxylic acid group of the resulting peptide can be deprotected by specific cleavage of one of its protecting groups (PGs), so that a subsequent coupling step can be carried out. LPPS is usually finalized by a global deprotection step, in which the remaining PGs are removed.

In certain embodiments of the invention, the peptide coupling reaction may be carried out using conventional process parameters and reagents typical for peptide coupling reactions.

The peptide coupling reaction may be carried out in a conventional manner by using a polar aprotic solvent and using one or more coupling reagents; preferably in the presence of one or more coupling additives and in the presence of one or more tertiary bases.

The coupling reagents used for the peptide coupling reaction are chosen so that they do not react with the polar aprotic solvent under the conditions of the peptide coupling reaction and so that no substantial epimerisation of the stereogenic center adjacent to the activated carboxylic acid group takes place. Preferred coupling reagents include phosphonium or uronium salts of O-1H-benzotriazole and carbodiimide coupling reagents.

Phosphonium and uronium salts are preferably selected from the group consisting of BOP (benzotriazol-1-yl-oxy-tris-(dimethylamino)-phosphonium hexafluorophosphate), PyBOP (benzotriazol-1-yl-oxy-trispyrrolidinophosphonium hexafluorophosphate), HBTU (O-(1H-benzotriazole-1-yl)-1,1,3,3-tetramethyluronium hexafluorophosphate), HCTU (O-(1H-6-chloro-benzotriazole-1-yl)-1,1,3,3-tetramethyluronium hexafluorophosphate), TCTU (O-(1H-6-chlorobenzotriazole-1-yl)-1,1,3,3-tetramethyluronium tetrafluoroborate), HATU (O-(7-azabenzotriazol-1-yl)-1,1,3,3-tetramethyluronium hexafluorophosphate), TATU (O-(7-azabenzotriazol-1-yl)-1,1,3,3-tetramethyluronium tetrafluoroborate), TBTU (O-(benzotriazol-1-yl)-1,1,3,3-tetramethyluronium tetrafluoroborate), TOTU (O-[cyano (ethoxycarbonyl)methyleneamino]-1,1,3,3-tetramethyluronium tetrafluoroborate), HAPyU (O-(benzotriazol-1-yl) oxybis-(pyrrolidino)-uronium hexafluorophosphate), PyAOP (benzotriazole-1-yl-oxy-tris-pyrrolidinophosphonium hexafluorophosphate), COMU (1-[(1-(cyano-2-ethoxy-2-oxoethylideneaminooxy)-dimethylamino-morpholinom-ethylene)]-methanaminium hexafluorophosphate), PyClock (6-chloro-benzotriazole-1-yl-oxy-tris-pyrrolidinophosphonium hexafluorophosphate), PyOxP (O-[(1-cyano-2-ethoxy-2-oxoethylidene)amino]-oxytri(pyrrolidin-1-yl)-phosphonium hexafluorophosphate) and PyOxB (O-[(1-cyano-2-ethoxy-2-oxoethylidene)amino]-oxytri(pyrrolidin-1-yl)-phosphonium tetrafluoroborate). Preferred coupling reagents selected from phosphonium or uronium coupling reagents are TBTU, TOTU and PyBOP.

Carbodiimide coupling reagents are preferably selected from the group consisting of diisopropyl-carbodiimide (DIC), dicyclohexyl-carbodiimide (DCC) and water-soluble carbodiimides (WSCDI) such as 1-ethyl-3-(3-dimethylaminopropyl)-carbodiimide (EDC). Water-soluble carbodiimides are more preferred as carbodiimide coupling reagents, whereby EDC is particularly useful.

The tertiary base employed in the peptide coupling reaction should be compatible with the peptide and with the coupling reagent and should not interfere with the process for extraction by acting as a surfactant. Preferably, the conjugated acid of said tertiary base used in the peptide coupling reaction has a pKa value from 7.5 to 15, more preferably from 7.5 to 10. The tertiary base is preferably selected from the group consisting of trialkylamines, such as N,N-diisopropylethylamine (DIPEA) or triethylamine (TEA), N,N-di-$C_{1-4}$ alkylanilines, such as N,N-diethylaniline, alkylpyridines, such as collidine (2,4,6-trimethylpyridine), or N—$C_{1-4}$ alkylmorpholines, such as N-methylmorpholine, with any $C_{1-4}$ alkyl being identical or different and independently from each other straight or branched $C_{1-4}$ alkyl. DIPEA, TEA and N-methylmorpholine are particularly useful as tertiary bases for the peptide coupling reaction.

A coupling additive is preferably a nucleophilic hydroxy compound capable of forming activated esters, more preferably having an acidic, nucleophilic N-hydroxy function wherein N is imide or is N-acyl or N-aryl substituted triazeno, the triazeno type coupling additive being preferably a N-hydroxybenzotriazol derivative (or 1-hydroxybenzotriazol derivative) or a N-hydroxybenzotriazine derivative. Preferred coupling additives are selected from the group consisting of N-hydroxysuccinimide (HOSu), 6-chloro-1-hydroxybenzotriazole (Cl-HOBO, N-hydroxy-3,4-dihydro-4-oxo-1,2,3-benzotriazine (HOOBt), 1-hydroxy-7-azabenzotriazole (HOAt), 1-hydroxybenzotriazole (HOBt) and ethyl-2-cyano-2-hydroxyiminoacetate (CHA). CHA is available under trade name OXYMAPURE®. CHA has proved to be an effective coupling additive as epimerisation of the stereogenic center of the activated carboxylic acid is suppressed to a higher degree in comparison to benzotriazole-based coupling additives. In addition, CHA is advantageous in that the coupling progress can be visually monitored by a color change of the reaction mixture. Preferably, HOBt is used as coupling additive for the peptide coupling reaction.

Preferably, from 0.9 to 5 mol equivalents, more preferably from 1 to 1.5 mol equivalents of coupling reagent is used, the mol equivalent being based on the mol of reactive C-terminal carboxylic acid groups. Preferably, from 0.1 to 5 mol equivalents, more preferably from 0.5 to 1.5 mol equivalents of coupling additive is used, the mol equivalent being based on the mol of coupling reagent. Preferably, from 1 to 10 mol equivalents, more preferably from 2 to 3 mol equivalents, of tertiary base is used, the mol equivalent being based on the mol of coupling reagent.

In the preferred embodiment of the present invention, the combination of reagents in the peptide coupling reaction is selected from the group consisting of TBTU/HOBt/DIPEA, PyBOP/TEA, EDC/HOBt and EDC/HOBt/DIPEA.

The reaction solvent for the peptide coupling reaction is selected from the group consisting of DCM, EtOAc, MeTHF, THF, CAN, DMF, DMA, NMP or mixtures thereof. Preferably, the reaction solvent is substantially water-free. The reaction solvent should contain less than 1 wt % water, preferably less than 0.1 wt % water, more preferably less than 0.01 wt % water and even more preferably less than 0.001 wt % water. The water content in a solvent can be determined by Karl Fischer titration according to the standard test method ASTM E203-8 as known in the prior art. Preferably, the reaction solvent for the peptide coupling reaction is substantially free of impurities such as primary and secondary amines, carboxylic acids and aliphatic alcohols. The reaction solvent for the peptide coupling reaction is considered to be substantially free of these impurities if less than 1 mol % of any of the starting materials used in substoichiometric or stoichiometric amount undergoes an undesired reaction with these impurities during the peptide coupling reaction.

The choice of the appropriate reaction temperature depends on the employed coupling reagent as well as on the stability of the peptide. Preferably, the peptide coupling reaction is carried out at a reaction temperature of from −15°

C. to 50° C., more preferably from −10° C. to 30° C., even more preferably from 0° C. to 25° C.

Preferably, the peptide coupling reaction is carried out at the atmospheric pressure. However, it is possible to carry out the peptide coupling reaction at a pressure which is higher or slightly lower than the atmospheric pressure.

The peptide coupling reaction can be carried out under an ambient atmosphere. However, an atmosphere of a protective gas such as nitrogen or argon is preferable.

In the present application, the term "reaction time" refers to the time required until the conversion of the reaction is substantially complete. The conversion of the reaction is considered to be substantially complete, once the amount of the starting material used in substoichiometric or stoichiometric amount decreases to less than 5 mol % of its initial amount, preferably to less than 2 mol % of its initial amount. The progress of the reaction can be monitored by analytical methods known in the art, for instance, by analytical high-performance liquid chromatography (HPLC), thin layer chromatography (TLC), mass spectrometry (MS) or HPLC-MS, whereby HPLC is particularly preferred for this purpose.

Preferably, the reaction time for the peptide coupling reaction ranges from 15 min to 20 h, more preferably from 30 min to 5 h, even more preferably from 30 min to 2 h.

Preferably, after the process for extraction, the organic layer containing the peptide is partially evaporated. In the present application, the obtained layer is thus designated as "partially evaporated organic layer". The temperature at which the partial evaporation takes place is not particularly limited and is chosen according to the thermal stability of the peptide. It is preferred that the partial evaporation of the organic layer is carried out at a temperature of from 30° C. to 50° C. In certain instances, the partial evaporation of the organic layer may be carried out under reduced pressure of from 20 mbar to 1000 mbar (20 hPa to 1000 hPa). A person skilled in the art is aware that the pressure at which the partial evaporation of the organic layer takes place is preferably adjusted according to the desired evaporation temperature.

In one of the embodiments of the invention, the organic layer containing the peptide is directly evaporated until dryness. Alternatively, the partial evaporation of the organic layer containing the peptide can be carried out, followed by an addition of toluene and a subsequent evaporation until dryness.

When LPPS is carried out on an industrial scale, the intermediate peptide is usually isolated by a direct precipitation from the reaction mixture after each coupling step, so that impurities, such as unreacted starting materials, side products as well as an excess of coupling reagents and bases, etc. can be separated. After the completion of the peptide coupling reaction, the reaction mixture is typically poured into an anti-solvent, such as e.g. diethyl ether, acetonitrile, diisopropyl ether, n-heptane, toluene or water, whereby the precipitation of the peptide takes place.

During the precipitation process it is desirable if at least 80 wt % of the peptide present in the partially evaporated organic layer precipitates as a solid material. It is preferred that at least 90 wt % of the peptide present in the partially evaporated organic layer precipitates as a solid material. It is even more preferred that at least 95 wt % of the peptide present in the partially evaporated organic layer precipitates as a solid material. It is particularly useful when at least 98 wt % of the peptide present in the partially evaporated organic layer precipitates as a solid material.

The temperature at which the precipitation process is carried out depends on the composition of the partially evaporated organic layer, choice of the anti-solvent and on the properties of the peptide.

The precipitation temperature has an influence on the completeness of the precipitation of the peptide and on the physical properties of the precipitated peptide. Preferably, the precipitation process is carried out at the precipitation temperature of from −10° C. to 60° C., whereby the precipitation temperature of from −10° C. to 30° C. is even more preferred. It is, however, particularly useful when the precipitation temperature ranges from −10° C. to 0° C.

Preferably, the precipitated peptide is separated by filtration and dried under reduced pressure. However, it is also possible to separate the precipitated peptide by centrifugation. If desired, the filtrate collected during the filtration can be subjected again to a partial evaporation and to a subsequent precipitation, so that a second batch of the precipitated peptide can be collected.

In another embodiment of the present invention, the partially evaporated organic layer containing the peptide is directly treated with a reagent cleaving one or several PGs of the peptide. For instance, the partially evaporated organic layer containing the peptide can be treated with an acidolytic reagent, whereby undesired reaction between the acidolytic reagent and polar aprotic solvent or inhibition of the cleavage is avoided. This embodiment of the present invention is particularly useful when the N-terminal PG of the peptide is tert-butoxycarbonyl (Boc) group.

In another embodiment of the present invention, the reagent cleaving one or several PGs of the peptide is added directly to the reaction mixture resulting from a peptide coupling reaction. After the cleavage of the targeted PG occurs, the resulting peptide is extracted from the reaction mixture. This embodiment of the present invention is particularly suitable when the N-terminal PG of the peptide is fluorenyl-9-methoxycarbonyl (Fmoc) group.

PGs and typical reaction conditions, parameters and reagents for cleaving PGs, which are conventionally used in the process for preparation of a peptide in liquid phase of the present invention, are known in the art. Protecting groups (PGs), be it for protecting functional groups in side chains of amino acids or peptides or for the protection of N-terminal amino groups or C-terminal carboxylic acid groups of amino acids or peptides, are for the purpose of the present invention classified into five different groups: 1. PGs cleavable under basic cleaving conditions, in the following called "basic type PGs", 2. PGs cleavable under strongly acidic cleaving conditions but not cleavable under mildly acidic cleaving conditions, in the following called "strong type PGs", 3. PGs cleavable under mildly acidic cleaving conditions, in the following called "weak type PGs", 4. PGs cleavable under reductive cleaving conditions, in the following called "reductive type PGs", and 5. PGs cleavable under saponification cleaving conditions, in the following called "saponification type PGs".

Basic cleaving conditions involve treatment of the peptide with a basic cleaving solution. As used herein, the basic cleaving solution comprises a mixture of basic reagent and a solvent. Basic reagents used in the present invention are secondary amines, preferably the basic reagent is selected from the group consisting of diethylamine (DEA), piperidine, 4-(aminomethyl)piperidine, tris(2-aminoethyl)amine (TAEA), morpholine, dicyclohexylamine, 1,3-cyclohexanebis(methylamine)-piperazine, 1,8-diazabicyclo[5.4.0]undec-7-ene and mixtures thereof. More preferably, the basic reagent used in the process for preparation of a peptide in liquid phase of the present invention is selected from the group consisting of DEA, TAEA and piperidine. The basic cleaving solution can also contain an additive, preferably selected from the group consisting of 6-chloro-1-hydroxy-benzotriazole, 1-hydroxy-7-azabenzotriazole, 1-hydroxybenzotriazole and ethyl-2-cyano-2-hydroxyiminoacetate and mixtures thereof.

In this section, the terms "part" and "wt %" in the description of basic, strongly acidic, mildly acidic and reductive cleaving conditions are meant to be a factor of the parts by weight of the peptide carrying the corresponding groups PG(s) which are being cleaved. For instance, the expression "5 parts of basic cleaving solution are used" means that 5 g of basic cleaving solution are used for the treatment of each 1 g of the peptide carrying a basic type PG. Preferably, from 5 to 20 parts, more preferably from 5 to 15 parts of basic cleaving solution are used. Preferably, the amount of basic reagent ranges from 1 to 30 wt %, more preferably from 10 to 25 wt %, even more preferably from 15 to 20 wt %, with the wt % being based on the total weight of the basic cleaving solution.

Strongly acidic cleaving conditions, as defined in the present invention, involve treatment of the peptide with a strongly acidic cleaving solution. The strongly acidic cleaving solution comprises an acidolytic reagent. Acidolytic reagents are selected from the group consisting of Bronsted acids, such as TFA, hydrochloric acid (HCl), aqueous hydrochloric acid (HCl), liquid hydrofluoric acid (HF) or trifluoromethanesulfonic acid, Lewis acids, such as trifluoroborate diethyl ether adduct or trimethylsilylbromid, and mixtures thereof.

The strongly acidic cleaving solution may comprise one or more scavengers, selected from the group consisting of dithiothreitol, ethanedithiol, dimethylsulfide, triisopropylsilane, triethylsilane, 1,3-dimethoxybenzene, phenol, anisole, p-cresol and mixtures thereof. The strongly acidic cleaving solution can also comprise water, a solvent or a mixture thereof, the solvent being stable under strong cleaving conditions.

Preferably, from 10 to 30 parts, more preferably from 15 to 25 parts, even more preferably from 19 to 21 parts of strongly acidic cleaving solution are used. The amount of acidolytic reagent can range from 30 to 350 wt %, preferably from 50 to 300 wt %, more preferably from 70 to 250 wt %, even more preferably from 100 to 200 wt %; with the wt % being based on the total weight of the strongly acidic cleaving solution. Preferably, from 1 to 25 wt % of total amount of scavenger is used, more preferably from 5 to 15 wt %, with the wt % being based on the total weight of the strongly acidic cleaving solution.

Mildly acidic cleaving conditions according to the present invention involve treatment of the peptide with a weakly acidic cleaving solution. The weakly acidic cleaving solution comprises an acidolytic reagent. The acidolytic reagent is selected from the group consisting of Bronsted acids, such as TFA, trifluoroethanol, hydrochloric acid (HCl), acetic acid (AcOH), mixtures thereof and/or with water.

Preferably, from 4 to 20 parts, more preferably from 5 to 10 parts, of weakly acidic cleaving solution are used. The amount of acidolytic reagent can range from 0.01 to 5 wt %, preferably from 0.1 to 5 wt %, more preferably from 0.15 to 3 wt %, with the wt % being based on the total weight of the weakly acidic cleaving solution.

Reductive cleaving conditions employed in certain embodiments of the invention involve treatment of the peptide with a reductive cleaving mixture. The reductive cleaving mixture may comprise a catalyst, a reducing agent and a solvent. The catalysts employed for the reductive cleaving conditions are selected from the group consisting of derivatives of Pd(0), derivates of Pd(II) and catalysts containing metallic palladium, preferably selected from the group consisting of $Pd[PPh_3]_4$, $PdCl_2[PPh_3]_2$, $Pd(OAc)_2$ and palladium on carbon (Pd/C). Pd/C is particularly preferred. The reducing agent is selected from the group consisting of $Bu_4N^+BH_4^-$, $NH_3BH_3$, $Me_2NHBH_3$, $tBu-NH_2BH_3$, $Me_3NBH_3$, HCOOH/DIPEA, sulfinic acids comprising $PhSO_2H$, $tolSO_2Na$ and $i-BuSO_2Na$ and mixtures thereof as well as molecular hydrogen; preferably the reducing agent is $tolSO_2Na$ or molecular hydrogen. The solvent employed under reductive cleaving conditions can be identical to the solvent present in the partially evaporated organic layer containing the peptide. Preferably, from 4 to 20 parts, more preferably from 5 to 10 parts, of a reductive cleaving solvent are used.

Saponification cleaving conditions involve treatment of the peptide with a saponification cleaving solution. The saponification cleaving solution may comprise a saponification reagent and a solvent. Saponification reagents used in the present invention are hydroxides of alkaline and earth alkaline metals, preferably the saponification reagent is selected from the group consisting of sodium hydroxide, lithium hydroxide and potassium hydroxide. More preferably, the saponification reagent used in the process for preparation of a peptide in liquid phase of the present invention is sodium hydroxide. The solvent of the saponification cleaving solution may comprise a mixture of water with a solvent selected from the group consisting of THF, MeTHF, ethanol, methanol and dioxane.

In certain embodiments of the invention, the basic type PGs are not cleavable under strongly acidic or mildly acidic cleaving conditions. Preferably, the basic type PGs are not cleavable under strongly acidic, weak or reductive cleaving conditions.

The term "strong type PGs" is understood to mean that the protecting groups are not cleavable under mildly acidic or basic cleaving conditions. Preferably, the strong type PGs are not cleavable under mildly acidic, basic or reductive cleaving conditions. Usually strong acidic PGs like Bzl are cleaved by hydrogenation. Typically, the global deprotection of a peptide is carried out by hydrogenation under very mild conditions.

Weak type PGs are not cleavable under basic cleaving conditions, but they are cleavable under strongly acidic cleaving conditions. Preferably, the weak type PGs are not cleavable under basic or reductive cleaving conditions, but they are cleavable under strongly acidic cleaving conditions.

According to one embodiment of the invention, the basic type PG is Fmoc. Preferably, the strong type PGs are selected from the group consisting of Boc, tBu, OtBu and Cbz. Preferably, the weak type PGs are selected from the group consisting of Trt and 2-chlorophenyldiphenylmethyl group. Preferably, the reductive type PGs are selected from the group consisting of Bzl, N-methyl-9H-xanthen-9-amino group and Cbz. Preferably, the saponification type PG is OMe.

In certain inventive processes for preparation of a peptide in liquid phase, the N-terminal PG of the peptide is removed in a deprotection reaction before the subsequent peptide coupling reaction is carried out.

The "N-terminal protecting group" is selected from the group consisting of Acr (acrylyl), Bz (benzoyl), Ac (acetyl), Trt (trityl), Boc (t-butyloxycarbonyl), CBz (benzyloxycarbonyl or Z), Dts (dithiasuccinoyl), Rdtc (R=Alkyl or Aryl, dtc=dithiocarbamate), DBFmoc (2,7-di-t-butylFmoc or 1,7- di-t-butylfluoren-9-ylmethoxycarbonyl), Alloc (allyloxycarbonyl), pNZ (p-nitrobenzyloxycarbonyl), Nsc ([[2-[(4-nitrophenyl)sulfonyl]ethoxy]carbonyl]), Msc (2-methylsulfonylethoxycarbonyl), MBz (4-methoxyCBz), Poc (2-phenylpropyl(2)-oxycarbonyl), Bpoc [(1-[1,1'-biphenyl]-4-yl-1-methylethoxy)carbonyl], Bnpeoc [[2,2-bis(4-nitrophenyl)ethoxy]carbonyl], CBz [(phenylmethoxy)carbonyl], Aoc [(1,1-dimethylpropoxy)carbonyl], and Moz [[(4-methoxyphenyl)methoxy]carbonyl]. Preferred N-terminal protecting groups are Fmoc, Bpoc, Trt, Poc and Boc. In certain inventive embodiments, the N-terminal PGs are preferably Fmoc, and Boc. For example, Fmoc is highly preferred for the LPPS as an N-terminal PG because it can be easily removed under basic conditions and the Fmoc, as a PG of the N-terminus of the peptide, is compatible with the side chain PGs in order to represent an orthogonal system. In another example, Boc is highly preferred as an N-terminal PG of the peptide for process for the preparation of a peptide in liquid phase because its removal can be carried out under strongly acidic conditions. As with Fmoc, usage of Boc PG of the N-terminus is also compatible with the side chain PGs in order to represent an orthogonal system.

In certain inventive embodiments, the C-terminal PG of the peptide is removed in the final deprotection step. Preferred C-terminal PGs are OtBu, Blz, OMe, $NH_2$, as well as 2-chlorophenyldiphenylmethylester or N-methyl-9H-xanthen-9-amide.

In certain inventive embodiments, it is desirable that the hydroxy-, amino-, thio- and carboxylic acid groups of the amino acids side chains of the peptide obtained by the process for preparation of a peptide in liquid phase are protected with suitable PGs, so that undesired side reactions are avoided. In addition, usage of the side chain PGs generally improves the solubility of the peptide in the polar aprotic solvents.

Generally, side chain PGs are chosen so that they are not removed during the deprotection of the N-terminal amino groups during the process for preparation of a peptide in liquid phase. Therefore, the PG of the N-terminal amino groups or C-terminal carboxylic acid groups and any side chain PG are typically different, preferably they represent an orthogonal system. Accordingly, preferred side chain groups include tBu, Trt, Boc, OtBu and Cbz.

Once the amino acid sequence of the peptide obtained by the process for preparation of a peptide in liquid phase is identical to the amino acid sequence of the target peptide, the N-terminal PG, the C-terminal PG and any side chain PG can be removed so that the unprotected target peptide is obtained. This step is called global deprotection. Preferably, the PGs used during the process for preparation of a peptide in liquid phase are selected to allow global deprotection under mildly acidic, strongly acidic or reductive cleaving conditions, as defined above, depending on the nature of PGs. Any side chain PGs are typically retained until the end of the LPPS. Global deprotection can be carried out under conditions applicable to the various side chain PGs.

Biotechnical Peptide Synthesis

The described peptides can also be produced by known biotechnical peptide synthesis methods, which involve the expression of the DNA encoding the peptide in a host cell. The DNA may be inserted into the downstream of a promoter in an appropriate expression vector to thereby produce a recombinant vector.

The recombinant vector is introduced into a host cell suitable for the expression vector to thereby obtain a transformant, which produces the described peptide. Any bacteria, yeasts, animal cells, insect cells, plant cells, and the like can be used as the host cell, so long as it can express the desired gene.

The expression vector includes those which can replicate autonomously in the above host cell or can be integrated into a chromosome and contain a promoter at such a position that the DNA encoding the described peptide can be transcribed.

When a procaryote, such as a bacterium or the like, is used as the host cell, it is preferred that the used recombinant DNA containing the DNA encoding the described peptide can replicate autonomously in the procaryot, and at the same time contain a promoter, a ribosome-binding sequence, the DNA of the described peptide and a transcription termination sequence. A gene regulating the promoter may also be contained.

The expression vector includes pBTrp2, pBTac1 and pBTac2 (all available from Boehringer Manheim), pKK223-3 (manufactured by Pharmacia), pSE280 (manufactured by Invitrogen), pGEMEX-1 (manufactured by Promega), pQE-8 (manufactured by QIAGEN), pKYP10, pKYP200, pLSA1, PGEL1, pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM B-400)], pGKA2 [prepared from *Escherichia coli* IGKA2 (FERM BP-6798)], pTerm2, pSupex, pUB110, pTPS, pC194, pEG400, pGEX (manufactured by Pharmacia), pET system (manufactured by Novagen), pSupex and the like.

Any promoter can be used, so long as it can function in the host cell. Examples include promoters derived from *Escherichia coli*, phage and the like, such as trp promoter ($P_{trp}$), lac promoter, $P_L$ promoter, $P_R$ promoter, T7 promoter and the like. Also, artificially designed and modified promoters, such as a promoter in which two $P_{trp}$ are linked in tandem ($P_{trp} \times 2$), tac promoter, lacT7 promoter leti promoter and the like, can be used.

It is preferred to use a plasmid in which the space between Shine-Dalgarno sequence, which is the ribosome binding sequence, and the initiation codon is adjusted to an appropriate distance (for example, 6 to 18 bases).

The nucleotides in the nucleotide sequence of the DNA encoding the described peptides may be substituted so as to have suitable codons for expression of the host to thereby improve the productivity of one or more desired peptides.

A transcription termination sequence is not always necessary for expression of the DNA. However, it is preferred to arrange the transcription terminating sequence just downstream of the structural gene.

The host cell includes microorganisms belonging to the genera *Escherichia, Serratia, Bacillus, Brevibacterium, Corynebacterium, Microbacterium, Pseudomonas* and the like. Examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium acetoacidophilum* ATCC 13870, *Hicrobacterium ammoniaphilum* ATCC 15354, *Pseudomonas* sp. D-0110 and the like.

Any suitable method for introducing the recombinant DNA into the above host cells can be used. Examples include a method using a calcium ion, a protoplast method, and the like.

When yeast is used as the host cell, the expression vector includes YEp13 (ATCC 37115), YEp24 (ATCC 37051), YCp50 (ATCC 37419) and the like. Any promoter can be used, so long as it can function in a yeast strain. Examples include a promoter of a gene in glycolytic pathway such as hexose kinase, etc., PHO5 promoter, PGK promoter, GAP promoter, ADH promoter, gal 1 promoter, gal 10 promoter, a heat shock polypeptide promoter, MFα1 promoter, CUP 1 promoter and the like. The host cell includes microorganisms belonging to the genera Saccharomyces, Schizosaccharomyces, Kluyveromyces, Trichosporon, Schwanniomyces, Pichia, Candida and the like. Examples include Saacharomyces cerevisiae, Schizosaccharomyces pombe, Kluyveromyces lactis, Trichosporon pullulans, Schwanniomyces alluvius and the like. Any suitable method for introducing the recombinant DNA into yeast can be used. Examples include electroporation, the spheroplast method, the lithium acetate method, and the like.

When an animal cell is used as the host cell, the expression vector includes pCDNAI and pcDM8 (available from Funakoshi), pAGE107, pAS3-3, pCDM8, pcDNAI/Amp (manufactured by Invitrogen), pREP4 (manufactured by Invitrogen), pAGE103, pAGE210 and the like. Any promoter can be used, so long as it can function in an animal cell. Examples include a promoter of IE (immediate early) gene of cytomegalovirus (CMV), an early promoter of SV40, a promoter of retrovirus, a metallothionein promoter, a heat shock promoter, SRα promoter and the like. Also, the enhancer of the IE gene of human CMV can be used together with the promoter. The host cell includes human Namalwa cell, monkey COS cell, Chinese hamster CHO cell, HBT5637 and the like. Any suitable method for introducing the recombinant DNA into an animal cell can be used. Examples include electroporation, a calcium phosphate method, lipofection and the like.

When an insect cell is used as the host cell, the described peptides can be expressed by any known method. A vector for introducing a recombinant gene and baculovirus are co-transfected into an insect cell to thereby obtain a recombinant virus in a supernatant in the culture of the insect cell, and then an insect cell is infected with the recombinant virus to thereby express the described peptide. The vector for introducing a gene used in the method includes pVL1392, pVL1393 and pBlueBacIII (all manufactured by Invitrogen) and the like. The baculovirus includes Autographa californica nuclear polyhedrosis virus which infects insects of the family Barathra and the like. The insect cell includes Spodoptera frugiperda ovary cells Sf9 and Sf21, Trichoplusia ni ovary cell High 5 (manufactured by Invitrogen) and the like. The method for co-transfecting the vector for transferring a recombinant DNA and the baculovirus for the preparation of the recombinant virus includes a calcium phosphate method, lipofection and the like.

When a plant cell is used as the host cell, the expression vector includes Ti plasmid, a tobacco mosaic virus vector and the like. Any promoter can be used, so long as it can be expressed in a plant cell. Examples include 35S promoter of cauliflower mosaic virus (CaMV), rice, actin 1 promoter and the like. The host cell includes plant cells such as tobacco, potato, tomato, carrot, soybean, rape, alfalfa, rice, wheat, barley, etc., and the like. Any suitable method for introducing recombinant DNA into a plant cell can be used. Examples include the Agrobacterium method, electroporation, the particle gun method and the like.

As the method for expressing the gene, secretion production, fusion protein expression and the like can be carried out according to known methods.

The described peptides can be produced by culturing the thus obtained transformant in a medium to thereby form and accumulate the peptide encoded by the DNA in the culture, and recovering it from the culture. The method for culturing the transformant in a medium is carried out according to conventional methods as used in culturing of the host.

As a medium for culturing the transformant obtained by using, as the host, prokaryote such as Escherichia coli or the like or eukaryote such as yeast or the like, the medium may be either a natural medium or a synthetic medium, so long as it contains a carbon source, a nitrogen source, inorganic salts and the like which can be assimilated by the organism and the transformant can be cultured efficiently. Any carbon source can be used, so long as the organism can be assimilated. Examples include carbohydrates such as glucose, fructose, sucrose, molasses containing them, starch, starch hydrolysate, etc., organic acids such as acetic acid, propionic acid, etc., alcohols such as ethanol, propanol, etc., and the like. The nitrogen source includes ammonia, various ammonium salts of inorganic acids or organic acids such as ammonium chloride, ammonium sulfate, ammonium acetate, ammonium phosphate, etc., other nitrogen-containing compounds, peptone, meat extract, yeast extract, corn steep liquor, casein hydrolysate, soybean meal and soybean meal hydrolysate, various fermented cells and hydrolysates thereof, and the like. The inorganic salts include potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing may be carried out under aerobic conditions by shaking culture, submerged spinner culture under aeration or the like. The culturing temperature is preferably from 15 to 40° C., and the culturing time is generally from 16 hours to 7 days. The pH is preferably maintained at 3.0 to 9.0 during culturing. The pH can be adjusted by using an inorganic or organic acid, an alkali solution, urea, calcium carbonate, ammonia or the like. Also, antibiotics such as ampicillin, tetracycline and the like can be added to the medium during culturing, if necessary.

When a microorganism transformed with a recombinant vector using an inducible promoter as a promoter is cultured, an inducer can be added to the medium, if necessary. For example, isopropyl-β-D-thiogalactopyranoside (IPTG) or the like can be added to the medium when a microorganism transformed with a recombinant vector using lac promoter is cultured, or indoleacrylic acid or the like can be added thereto when a microorganism transformed with a recombinant vector using tip promoter is cultured.

The medium for culturing a transformant obtained using an animal cell as the host includes generally used RPMI 1640 medium, Eagle's MEM, modified Dulbecco's MEM, 199 Medium, and other media to which fetal calf serum or the like has been added to the above media and the like. Culturing is generally carried out at pH 6 to 8 and at 30 to 40° C. in the presence of 5% $CO_2$ for 1 to 7 days. Furthermore, antibiotics such as kanamycin, penicillin and the like can be added to the medium during culturing, if necessary.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium and the like. Culturing is generally carried out at pH 6 to 7 and at 25 to 30° C. for 1 to 5 days. Furthermore, antibiotics such as gentamicin and the like may be added to the medium during culturing, if necessary.

A transformant obtained by using a plant cell as the host can be used as the cell or after differentiating to a plant cell or organ. The medium used in culturing of the transformant includes Murashige and Skoog (MS) medium, White medium, media to which a plant hormone such as auxin, cytokinine or the like has been added, and the like. Culturing is carried out generally at a pH 5 to 9 and at 20 to 40° C. for 3 to 60 days. Furthermore, antibiotics such as kanamycin, hygromycin and the like can be added to the medium during culturing, if necessary.

As indicated above, the described peptides can be produced by culturing a transformant derived from a microorganism, an animal cell or a plant cell containing a recombinant DNA to which a DNA encoding the peptide has been inserted, according to conventional culturing methods to form and accumulate the peptide, and recover the peptide from the culture.

The process for producing the described peptides includes a method of intracellular production in a host cell, a method of extracellular secretion from a host cell, and a method of production on an outer membrane of the host cell. The method can be selected by changing the used host cell or the structure of the produced peptide encoded by DNA of the described peptides.

When the described peptide is produced in a host cell or on an outer membrane of the host cell, the peptide can be secreted extracellularly according to known methods.

That is, such a peptide can be secreted extracellularly by expressing it in the form that a signal peptide has been added just before the active site of the peptide in the peptide encoded by the DNA according to the recombinant DNA technique.

Furthermore, the amount of production can be increased using a gene amplification system, such as a dihydrofolate reductase gene or the like according to known methods.

Moreover, the described peptides can be produced by redifferentiating animal or plant cells to which the gene has been introduced to prepare a gene-introduced animal individual (transgenic non-human animal) or plant individual (transgenic plant) and using the individuals.

When the transformant is the animal individual or plant individual, the peptide can be produced by breeding or cultivating it so as to form and accumulate the peptide, and recovering the peptide from the animal individual or plant individual.

The process for producing the described peptides using the animal individual includes a process for producing the protein in an animal developed by introducing a gene according to known methods. In the animal individual, for example, the peptide can be produced by breeding a transgenic non-human animal to which the DNA of the peptide has been introduced to form and accumulate this peptide encoded by the DNA in the animal, and recovering the resulting peptide from the animal. The peptide thus produced can be accumulated in milk, egg and the like of the animal. Any promoter can be used, so long as it can be expressed in the animal. Suitable examples include an α-casein promoter, a β-casein promoter, a β-lactoglobulin promoter, a whey acidic protein promoter, and the like, which are specific for mammary glandular cells.

A method for producing the described peptide using the plant individual includes a method for producing the described peptide by cultivating a transgenic plant to which the DNA of the described peptide is introduced, by a known method to form and accumulate the peptide encoded by the DNA in the plant, and recovering the resulting peptide from the plant.

When the peptide produced by the transformant is expressed as a soluble product in cells, the cells are collected by centrifugation after culturing, suspended in an aqueous buffer, and disrupted using an ultrasonicator, a French press, a Manton Gaulin homogenizer, a Dynomill, or the like to obtain a cell-free extract. From the supernatant obtained by centrifuging the cell-free extract, a purified product can be obtained by the usual method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-S pharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis such as isoelectronic focusing or the like, alone or in combination thereof.

When the peptide is expressed as an inclusion body in the host cells, the cells are collected in the same manner, disrupted and centrifuged to recover the peptide as the precipitate fraction. Next, the inclusion body of the peptide is solubilized with a protein-denaturing agent. The solubilized solution is diluted or dialyzed to reconstitute the normal tertiary structure of the peptide, which is subjected to the purification and isolation method similar to the above to obtain the purified product of the peptide.

When the described peptide is extracellularly secreted, the peptide can be collected in the culture supernatant. Specifically, the culture supernatant is obtained by treating the culture in a treatment similar to the above, such as centrifugation or the like, and a purified product can be obtained from the supernatant using a purification and isolation method similar to the above.

The described peptide can be produced in the form of salts according to the conditions in the above production method. The salts of such a peptide are suitable for use in foods and beverages, and include acid addition salts, metal salts, and organic base addition salts. The acid addition salts include inorganic acid salts such as hydrochloride, sulfate, phosphate and the like, and organic acid salts such as acetate, maleate, fumarate, tartarate, citrate and the like the metal salts include alkali metal salts such as sodium salts, potassium salts, etc.; alkaline earth metal salts such as magnesium salts, calcium salts, etc.; aluminum salts, zinc salts and the like. The organic base addition salts include salts formed with a primary amine such as methylamine, ethylamine, aniline, etc., a secondary amine such as dimethylamine, diethylamine, pyrrolidine, piperidine, morpholine, piperazine, etc.; or a tertiary amine such as trimethylamine, triethylamine, N,N-dimethylaniline, pyridine, etc.; ammonium salts; and the like.

The salts can be prepared using an appropriate acid such as hydrochloric acid or the like or an appropriate base such as sodium hydroxide. For example, the salts can be prepared by a treatment according to the standard protocol in water or liquid containing an inactive water-miscible organic solvent such as methanol, ethanol or dioxane. Also, the treatment temperature is 0 to 100° C., preferable room temperature.

Moreover, the biochemical and physicochemical properties of the described peptides can be analyzed by mass spectrometry, nuclear magnetic resonance, electrophoresis, high performance liquid chromatography or the like.

Having generally described the invention, the same will be more readily understood by reference to the following examples, which are provided by way of illustration and are not intended as limiting. Without further description, it is believed that one of ordinary skill in the art can, using the preceding description and the following illustrative examples, make and utilize the alterations detected in the present invention and practice the claimed methods. The following working examples therefore, specifically point out preferred embodiments of the invention, and are not to be construed as limiting in any way the remainder of the disclosure.

Example 1: Peptide Preparation

The following six peptides (>95% purity) were ordered from EZBiolab Inc. located at 1033 3$^{rd}$ Avenue SW, Carmel, Ind. 46032, USA.

Pro-Thr-Pro-Leu-Leu (Ia),

Pro-Thr-Pro-Leu-Leu-NH$_2$ (Ib),

Pro-Pro-Thr-Leu-Leu (Ic),

Leu-Ala-Cys-His-Leu-Leu (Id),

Glu-Glu-Leu-Leu-Pro-Glu (Ie), and

His-Ser-Leu-Leu-Val-Pro (If).

Example 2: Peptide Composition

A peptide composition was prepared by mixing the six peptides (Ia), (Ib), (Ic), (Id), (Ie) and (If) from Example 1 in a weight ratio of 1:1:1:1:1:1.

Example 3: Peptide Composition

A peptide composition was prepared by mixing the three peptides (Ic), (Ie) and (If) from Example 1 in a weight ratio of 1:1:1.

Example 4: Peptide as Coffee Additive

Coffee brews were prepared using a commercially available roast and ground coffee product (FOLGERS® brand Classic Decaf coffee) using a standard automatic drip coffee brewer (i.e., MR. COFFEE®). The brewing process was carried out as instructed on the coffee package. Each single peptide in Example 1 and peptide compositions in Examples 2 and 3 were mixed into to the coffee brew. Five expert panelists evaluated the effect of peptide additive on coffee flavor profile. Round panel discussion resulted in the evaluations as tabulated below.

| Additive | Concentration of additive in coffee brew (ppm) | Sensory Evaluation |
| --- | --- | --- |
| None | 0 | Control |
| Peptide (Ia) | 40 | Stronger than control, very bitter |
| Peptide (Ib) | 40 | Similar to control |
| Peptide (Ic) | 40 | Stronger than control, bitter aftertaste, not as strong as (Ia) |
| Peptide (Id) | 40 | Strange non-coffee taste charcoal, cigar, smoky |
| Peptide (Ie) | 40 | Stronger than control, fuller |
| Peptide (If) | 40 | Similar to (Ie), a little more full/rounded |
| Example 2 Composition | 40 | More full and rounded than samples containing individual peptide |
| Example 3 Composition | 40 | Better than Example 2 Composition, Highest increase in perceived strength; full and rounded flavor |

Example 5: Peptide Composition of Example 3

Similar to Example 4, coffee brews were prepared from commercially available coffee products (FOLGERS® brands Classic Decaf roast and ground coffee, Classic Instant coffee, and Colombian Liquid Coffee Concentrate). The peptide composition from Example 3 was added to these coffee brews at different levels. Round panel discussion resulted in the evaluations as tabulated below.

| | Concentration of Example 3 Peptide Composition | | |
| --- | --- | --- | --- |
| Coffee Type | 4 ppm | 20 ppm | 40 ppm |
| Folgers Classic Decaf | Mild strength improvement | Medium strength improvement, mild lingering and slow roast notes | Strong strength improvement, strong lingering and slow roast notes |
| Folgers Classic Instant | Mild strength improvement | Medium strength improvement, mild lingering and slow roast notes | Strong strength improvement, strong lingering and slow roast notes |
| Colombian Liquid Concentrate | Mild strength improvement | Medium strength improvement, mild lingering and slow roast notes | Strong strength improvement, strong lingering and slow roast notes, and diminished extraction note |

It should be understood that while the invention has been described in conjunction with the detailed description thereof, the foregoing description is merely intended to illustrate and not to limit the scope of the invention, which is defined by the scope of the appended claims. It is contemplated that other aspects, advantages, and modifications are also within the scope of the claims as provided herein.

The invention claimed is:

1. A peptide consisting essentially of an amino acid sequence selected from the group consisting of:
SEQ ID NO: 1 Pro-Thr-Pro-Leu-Leu,
SEQ ID NO: 2 Pro-Thr-Pro-Leu-Leu-NH$_2$,
SEQ ID NO: 3 Pro-Pro-Thr-Leu-Leu,
SEQ ID NO: 4 Leu-Ala-Cys-His-Leu-Leu,
SEQ ID NO: 5 Glu-Glu-Leu-Leu-Pro-Glu, and
SEQ ID NO: 6 His-Ser-Leu-Leu-Val-Pro.

2. A peptide composition comprising two or more different peptides, each of which peptides consists essentially of an amino acid sequence selected from the group consisting of
SEQ ID NO: 1,
SEQ ID NO: 2,
SEQ ID NO: 3,
SEQ ID NO: 4,
SEQ ID NO: 5, and
SEQ ID NO: 6.

3. The peptide composition according to claim 2, which comprises SEQ ID NO: 1, SEQ ID NO: 5, and SEQ ID NO: 6.

4. The peptide composition according to claim 3, wherein the weight ratio between SEQ ID NO: 1, SEQ ID NO: 5, and SEQ ID NO: 6 is represented by 1:m:n, wherein $0.5 \leq m \leq 2$, and $0.5 \leq n \leq 2$.

5. The peptide composition according to claim 4, wherein m=1, and n=1.

6. The peptide composition according to claim 2, which comprises SEQ ID NO: 1, SEQ ID NO: 2, SEQ ID NO: 3, SEQ ID NO: 4, SEQ ID NO: 5, and SEQ ID NO: 6.

7. The peptide composition according to claim 6, wherein the weight ratio between SEQ ID NO: 1, SEQ ID NO: 2, SEQ ID NO: 3, SEQ ID NO: 4, SEQ ID NO: 5, and SEQ ID NO: 6 is represented by 1:p:q:r:s:t, wherein $0.8 \leq p \leq 1.2$, $0.8 \leq q \leq 1.2$, $0.8 \leq r \leq 1.2$, $0.8 \leq s \leq 1.2$, and $0.8 \leq t \leq 1.2$.

8. The peptide composition according to claim 7, wherein p=1, q=1, r=1, s=1, and t=1.

9. A food or beverage product comprising one or more peptides consisting essentially of an amino acid sequence selected from the group consisting of:
SEQ ID NO: 1,
SEQ ID NO: 2,
SEQ ID NO: 3,
SEQ ID NO: 4,
SEQ ID NO: 5, and
SEQ ID NO: 6.

10. The food or beverage product according to claim 9, which is selected from alcoholic and non-alcoholic ready to drink and dry powdered beverages.

11. The food or beverage product according to claim 9, which is selected from tea, roast and ground coffee, coffee brew, and coffee creamer.

12. The food or beverage product according to claim 9, which is selected from instant coffee, liquid coffee concentrate, and decaf coffee.

13. The food or beverage product according to claim 9, which is a coffee brew made from instant coffee, liquid coffee concentrate, or decaf coffee.

14. The food or beverage product according to claim 9, wherein the total amount of the peptide(s) in the coffee brew is in the range of from about 4 ppm to about 40 ppm by weight.

* * * * *

UNITED STATES PATENT AND TRADEMARK OFFICE
CERTIFICATE OF CORRECTION

PATENT NO. : 10,005,816 B2
APPLICATION NO. : 14/569911
DATED : June 26, 2018
INVENTOR(S) : Jessalin Anise Howell et al.

Page 1 of 1

It is certified that error appears in the above-identified patent and that said Letters Patent is hereby corrected as shown below:

On the Title Page

In Item (54), before "PEPTIDES AND THEIR USE IN FOOD AND BEVERAGE", insert --NOVEL--.

In Item (57), ABSTRACT, Line 2, delete "comprising" and insert --having--.

Signed and Sealed this
Twenty-eighth Day of May, 2019

Andrei Iancu
*Director of the United States Patent and Trademark Office*